(12) United States Patent
Gambacorta

(10) Patent No.: US 7,303,393 B2
(45) Date of Patent: Dec. 4, 2007

(54) ARTICULATOR SYSTEM

(76) Inventor: Enzo Gambacorta, 239 Harrison Ave., Harrison, NY (US) 10528

( * ) Notice: Subject to any disclaimer, the term of this patent is extended or adjusted under 35 U.S.C. 154(b) by 0 days.

(21) Appl. No.: 11/355,337

(22) Filed: Feb. 16, 2006

(65) Prior Publication Data

US 2007/0190480 A1    Aug. 16, 2007

(51) Int. Cl.
*A61C 11/00* (2006.01)
(52) U.S. Cl. ...................................................... 433/60
(58) Field of Classification Search ................ 433/60, 433/54, 53, 61, 64, 65, 57, 63
See application file for complete search history.

(56) References Cited

U.S. PATENT DOCUMENTS

| | | | | |
|---|---|---|---|---|
| 750,203 | A * | 1/1904 | Knight | 433/64 |
| 3,018,551 | A * | 1/1962 | Weiss | 433/61 |
| 4,378,929 | A * | 4/1983 | Huffman | 249/124 |
| 4,460,338 | A * | 7/1984 | Mercer et al. | 433/60 |
| 6,234,794 | B1 * | 5/2001 | Ozaki | 433/57 |
| 6,386,868 | B1 * | 5/2002 | Fujita | 433/60 |

* cited by examiner

*Primary Examiner*—Cris Rodriguez
*Assistant Examiner*—Sunil K. Singh

(57) ABSTRACT

An articulator system employing magnetic and supporting means enabling dental casts to be mounted in or removed from an articulator and replaced as desired.

1 Claim, 2 Drawing Sheets

ARTICULATOR SYSTEM

FIELD OF THE INVENTION

This invention is directed toward articulators or work support apparatus for use by dentists, dental laboratory technicians and others in evaluating and supporting dental casts of upper and lower molded teeth of dental patients.

BACKGROUND OF THE INVENTION

It often necessary for dentists in evaluating teeth of patients to prepare molds of upper and lower teeth and send them to dental laboratories that will prepare dental casts of these upper and lower molds and assemble them together to display the resultant combination of temporarily joined casts. Typically the molds are joined together in a device known as an articulator.

An articulator employs a vertical support of some type with upper and lower spaced horizontal metallic plates movable toward and away from each other, with the cast of the lower teeth being secured to the lower surface of the lower plate and the cast of the upper teeth being secured to the upper surface of the upper plate.

In order to insure that the casts are properly secured to the plates, plaster is used normally and subsequent removal is very difficult. Once casts are employed in this manner, they cannot be remounted in an articulator without breaking off the plaster.

The present invention overcomes this problem by eliminating this use of plaster and instead using a novel articulator system that enable casts to be repeatedly remounted in articulators at any time.

SUMMARY OF THE INVENTION

It is a primary object of this invention to provide a novel articulator system which enables dental casts to be repeatedly removed and reinstalled in one or another positions instantly according to the bite site registration.

Another important object of this invention is to provide an articulator system of the character indicated which employs a novel use of supporting means in enabling dental casts to be removed and replaced as desired.

These and other objects and advantages of this invention will either be explained or will become apparent hereafter.

An articulator in accordance with the principles of this invention takes the form of a vertical frame having two identical spaced parallel vertical columns adjustable in length.

A first horizontal elongated member extending between and is connected to the upper ends of the columns, said first member having an extension disposed at right angles to the direction of elongation of the first member.

A horizontal elongated bar is supported on the first member, said bar extending between and interconnecting the upper ends of the columns.

A second horizontal elongated member extends between the lower ends of the columns and supports them. The second member has an extension disposed at right angles to the direction of elongation of the second member. The extensions of the first and second members are parallel and vertically aligned.

A first horizontal upper elongated metallic plate extends over the horizontal extension of the first member and has a coupling at one end, said first plate having a magnet disposed therein.

First means is connected to said bar and is disposed over the first extension, said first means being also connected to the coupling of said first plate as a locking device so that the first plate is pivotable about a horizontal axis that is disposed at right angles to the axis of the bar and the plate cannot move along the horizontal axis.

A second horizontal lower elongated metallic plate extends outward parallel to the horizontal extension and is disposed below the first plate, said second plate having a coupling at one end, said second plate having a magnet disposed therein.

Second means is connected to the second member and is also connected to the coupling of said second plate as a locking device so that the second plate is pivotable about a horizontal axis which is disposed at right angles to the axis of the bar and the plate cannot move along the horizontal axis.

Each plate can also be provided with supporting means which can take the form of a plurality of holes disposed about the corresponding magnet.

Each of the first and second plates is adapted to engage a corresponding one of first and second dental casts. Each cast has an exposed metallic sheet containing a like plurality of raised prongs whereby upon magnetic engagement between plate and magnet, each prong engages the corresponding hole.

DETAILED DESCRIPTION OF PREFERRED EMBODIMENTS

Figure 1:
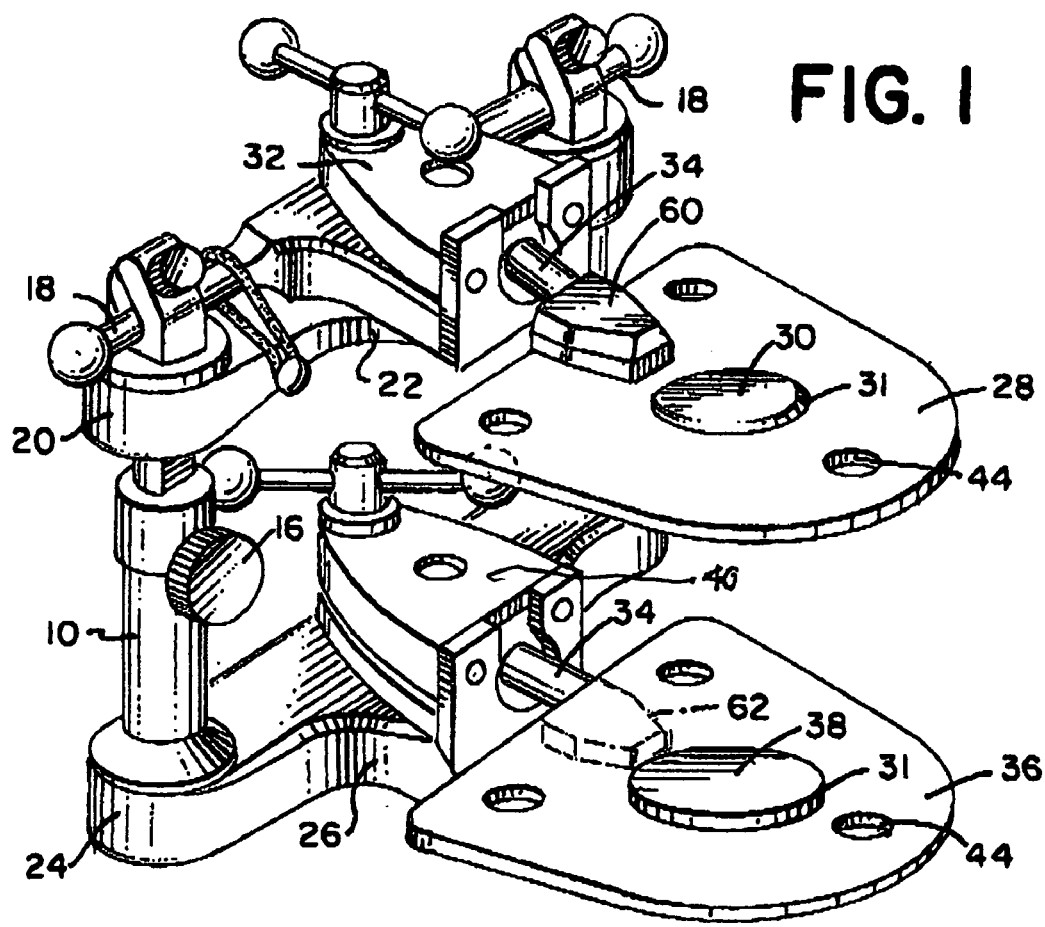
FIG. 1 is a perspective view of a preferred embodiment of the invention.
Figure 2:
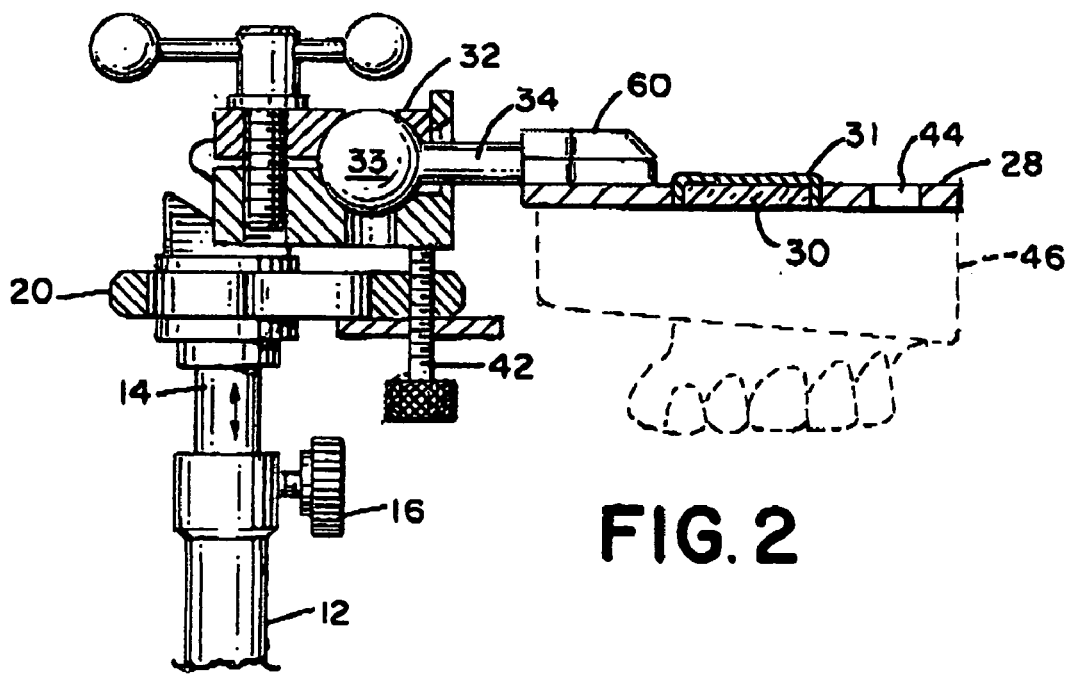
FIG. 2 is a detail side view of the structure shown in FIG. 1.
Figure 3:
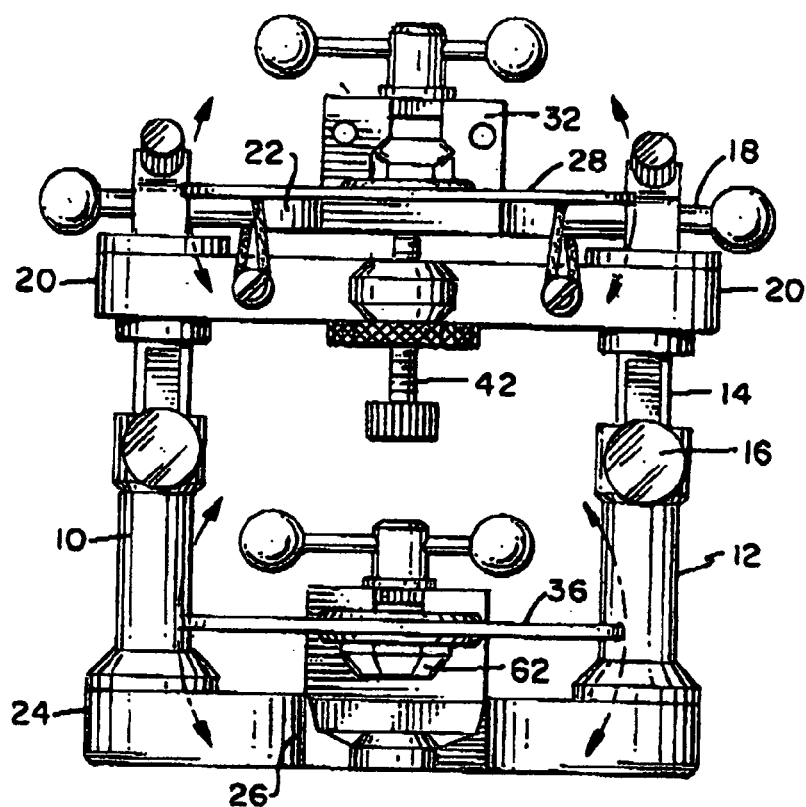
FIG. 3 is a front view of the structure shown in FIG. 1.
Figure 4:
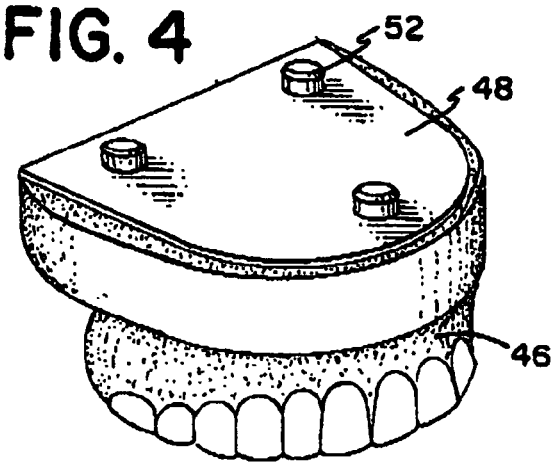
FIG. 4 is a perspective view of a dental cast which can be removably mounted in the structure shown in the FIGS. 1-3.

Referring now to FIGS. 1-5, the articulator has a vertical frame having two identical spaced parallel vertical columns 10 and 12. Each column is hollow and contains a shaft 14 which can be extended and manually locked into position by screws 16 to adjust the height as desired.

A horizontal bar 18 extends between and interconnects the upper ends of the columns or the shafts 14 if shafts are extended. A flat horizontal member 20 is disposed below the bar 18 and has an extension 22 which is oriented at right angles to bar 18. A second like member 24 supports the bottom end of the columns and has a like extension 26. Extensions 22 and 24 are spaced apart in parallel alignment.

A first horizontal upper elongated metallic plate 28 extends over the first horizontal member 20. It has a coupling 60 at one end and has a housing 31 in which a magnet 30 is mounted.

A first housing 32 contains a ball bearing 33 and attached shaft 34 that is connected to said bar and is disposed over the first extension, said shaft being also connected to the coupling 60 of said first plate as a locking device so that the first plate is pivotable about a horizontal axis that is disposed at right angles to the axis of the bar and the plate cannot move along the horizontal axis.

A second horizontal lower elongated metallic plate 36 extends outward parallel to the horizontal extension 26 and is disposed below the first plate. The second plate has a coupling 62 at one end and has a housing in which magnet 38 is mounted A second housing 40 connected to the top surface of member 24 is connected by a ball bearing 33 and shaft 34 to coupling 62 of the second plate 32 as a locking device so that the second plate is pivotable about shaft 34 that is disposed at right angles to the axis of the horizontal bar 18 and the plate cannot move along this axis.

A set screw arrangement 42 is connected to the bottom of the first housing to limit the downward movement of the first plate.

Figure 5:
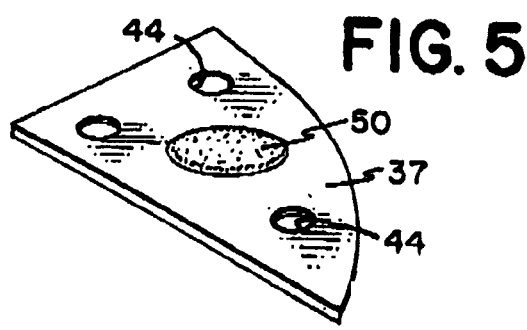
FIG. 5 is a plan view of different sizes of different plates that can be employed in this invention.

Plate 37 can be individually reversed in position to be left or right quadrants. As shown in FIG. 5, plate 37 has magnet 50.

Each of plates 28, 36 and 37 has a plurality of holes 44 disposed about the corresponding magnet.

Each of the first, second and third plates is adapted to engage a corresponding one of first and second dental casts 46. Each cast 46 has an exposed metallic sheet 48 surrounded by a like plurality of raised prongs 52 whereby upon magnetic engagement between plate and sheet each prong engages the corresponding hole.

The casts can be easily removed manually or replaced as desired.

While the invention has been carefully described with reference both to the detailed description and the drawings, the protection solicited should be limited only by the terms of the claims that follow.

What is claimed is:

1. An articulator system comprising:
   a vertical frame having two identical spaced parallel vertical columns adjustable in length;
   a first horizontal elongated member extending between and connected to the upper ends of the columns, said first member having a first horizontal extension disposed at right angles to the direction of elongation of the first member;
   a horizontal bar supported on the first member, said bar extending between and interconnecting the upper ends of the columns, said horizontal bar being rotatable about its horizontal axis,
   a second horizontal elongated member extending between the lower ends of the columns and supporting them, said second member having a second horizontal extension disposed at right angles to the direction of elongation of the second member, the first and second horizontal extensions of the first and second members being parallel and vertically aligned;
   a first horizontal upper elongated metallic plate extending over the first horizontal extension of the first member, said first plate having a first coupling at one end and having a first magnet disposed thereon;
   a first housing containing a first ball bearing and first attached horizontal shaft that is connected to said bar, the first housing being disposed over the first extension, said first shaft being connected to the first coupling of the first plate as a locking device so that the first plate is pivotable about a horizontal axis which is disposed at right angles to the axis of the bar and the first plate cannot move along the axis of the bar;
   a second horizontal lower elongated metallic plate extending outward parallel to the second horizontal extension of the second member and disposed below the first plate, said second plate having a second magnet disposed thereon and having a second coupling at one end;
   a second housing containing a second ball bearing and second horizontal attached shaft that is connected to said second horizontal member, the second housing being disposed over the second extension, said second shaft being connected to the second coupling of said second plate as a locking device so that that the second plate is pivotable about a horizontal axis which is disposed at right angles to the axis of the bar and the second plate cannot move along the axis of the bar; wherein the first plate has a plurality of holes disposed about the first magnet and the second plate has a plurality of holes disposed about the second magnet;
and wherein the articulator system further comprises a first and a second dental cast;
the first cast being disposed below the first plate of the articulator and having a first exposed upper metallic sheet having a first plurality of raised prongs so that the prongs will engage will engage the holes surrounding the first magnet and the sheet will be secured to the first plate by action of the first magnet to secure the first cast to the first plate; and
the second cast being disposed above the second plate of the articulator and having a second exposed lower metallic sheet having a second plurality of raised prongs so that the prongs will engage the holes surrounding the second magnet and the sheet will be secured to the second plate by action of the second magnet to secure the second cast to the second plate.

* * * * *